United States Patent
Feng et al.

(10) Patent No.: US 11,406,622 B2
(45) Date of Patent: Aug. 9, 2022

(54) GLAUCOCALYXIN A DERIVATIVE, PHARMACEUTICALLY ACCEPTABLE SALT THEREOF, OR PHARMACEUTICAL COMPOSITION THEREOF AND USES THEREOF IN PREPARATION OF DRUGS FOR TREATING PSORIASIS

(71) Applicant: SUZHOU PHARMAVAN CO., LTD., Suzhou (CN)

(72) Inventors: Haimei Feng, Suzhou (CN); Rensen Zhou, Suzhou (CN); Yunhui Yu, Suzhou (CN); Chuanliang Jiang, Suzhou (CN); Shiping Deng, Suzhou (CN); Qian Liu, Suzhou (CN)

(73) Assignee: SUZHOU PHARMAVAN CO., LTD., Jiangsu (CN)

( * ) Notice: Subject to any disclaimer, the term of this patent is extended or adjusted under 35 U.S.C. 154(b) by 215 days.

(21) Appl. No.: 16/488,048

(22) PCT Filed: Feb. 2, 2018

(86) PCT No.: PCT/CN2018/075061
§ 371 (c)(1),
(2) Date: Aug. 22, 2019

(87) PCT Pub. No.: WO2018/153235
PCT Pub. Date: Aug. 30, 2018

(65) Prior Publication Data
US 2020/0061029 A1  Feb. 27, 2020

(30) Foreign Application Priority Data
Feb. 23, 2017 (WO) ................ PCT/CN2017/074538

(51) Int. Cl.
*A61K 31/428* (2006.01)
*A61P 17/06* (2006.01)

(52) U.S. Cl.
CPC ............ *A61K 31/428* (2013.01); *A61P 17/06* (2018.01)

(58) Field of Classification Search
None
See application file for complete search history.

(56) References Cited

U.S. PATENT DOCUMENTS

2018/0079711 A1   3/2018  Feng et al.

FOREIGN PATENT DOCUMENTS

| CN | 1541643 A | 11/2004 |
|---|---|---|
| CN | 104356090 A | 2/2015 |
| CN | 104761460 A | 7/2015 |
| CN | 104887652 A | 9/2015 |
| JP | 2006524659 A | 11/2006 |
| JP | 2018514514 A | 6/2018 |
| WO | 2016150207 A1 | 9/2016 |
| WO | 2016150208 A1 | 9/2016 |

OTHER PUBLICATIONS

Berge et al., "Pharmaceutical Salts", Journal of Pharmaceutical Sciences, vol. 66(1), pp. 1-19. (Year: 1977).*
Japanese-language Notice of Reasons for Refusal issued in counterpart JP Application No. 2019-537224 dated Jun. 12, 2020 with English translation.
Extended European Search Report issued in counterpart EP Application No. 18758035.2 dated Jul. 28, 2020.
Chinese-language First Office Action issued in counterpart CN Application No. 201880009428.9 dated Nov. 24, 2021, with English translation (eighteen (18) pages).
Bian, Gang et al. 2021. "DGT, a novel heterocyclic diterpenoid, effectively suppresses psoriasis via inhibition of STAT3 phosphorylation." Br J Pharmacol. vol. 178, p. 636-653.

* cited by examiner

*Primary Examiner* — Savitha M Rao
*Assistant Examiner* — Gregg Polansky
(74) *Attorney, Agent, or Firm* — David S. Bradin; Nexsen Pruet, PLLC (57) ABSTRACT

A glaucocalyxin A derivative, a pharmaceutically acceptable salt thereof, or a pharmaceutical composition thereof and uses thereof in the preparation of drugs for treating psoriasis.

18 Claims, 1 Drawing Sheet

GLAUCOCALYXIN A DERIVATIVE, PHARMACEUTICALLY ACCEPTABLE SALT THEREOF, OR PHARMACEUTICAL COMPOSITION THEREOF AND USES THEREOF IN PREPARATION OF DRUGS FOR TREATING PSORIASIS

CROSS REFERENCE TO RELATED APPLICATION

The present application is the U.S. national stage entry, under 35 U.S.C. 371, of PCT Application PCT/CN2018/075061, entitled "Glaucocalyxin A Derivative, Pharmaceutically Acceptable Salt Thereof, Or Pharmaceutical Composition Thereof And Uses Thereof In Preparation Of Drugs For Treating Psoriasis," filed on Feb. 2, 2018, which in turn claims priority to PCT/CN2017/074538, filed Feb. 23, 2017, the contents of each of which are hereby incorporated by reference in their entirety, for all purposes.

TECHNICAL FIELD

The present application belongs to the field of chemical medicine, and relates to a glaucocalyxin A derivative, and a pharmaceutically acceptable salt thereof, or a pharmaceutical composition comprising the same, and use thereof in the preparation of a medicament for treating psoriasis.

BACKGROUND

Psoriasis is a common, chronic, relapsing, inflammatory skin disease that seriously affects the quality of life of patients. Patients with psoriasis have an increased prevalence of cardiovascular disease, diabetes, hypertension, hyperlipidemia, obesity, intestinal infection, obstructive sleep apnea, steatohepatitis, and psychosis. According to clinical manifestations, psoriasis can be divided into four types: psoriasis vulgaris, arthritic psoriasis, pustular psoriasis, and erythrodermic psoriasis. Psoriasis vulgaris accounts for more than 90% of psoriasis cases. The exact etiology and pathogenesis of psoriasis remain unclear. Psoriasis affects 2-4% of the world's population, and the clinical symptoms thereof are represented by thickened plaques that can cause systemic pain, local dull pain, and itchy skin. The rash may be in the form of a drop, a coin, a map, a mixture, and the like. Patients with psoriasis have a lower quality of life than that of ordinary people, and they have an increased risk of developing concurrent multiple diseases.

As seen from the above, psoriasis seriously harms the health of patients, and therefore it is of great significance to find effective drugs for treating psoriasis. Although there are currently various kinds of drugs useful for treating psoriasis, it is difficult for most patients to insist on the drug treatment due to the factors such as complex mechanisms of such drugs, the long treatment period, and the relapse of the disease induced by environmental factors. Therefore, there is an urgent need to develop a new therapeutic drug with rapid curative effects, more safety and tolerance, few side effects, and improved patient compliance.

CN104356090A discloses a thiazole derivative of glaucocalyxin A, a preparation method thereof, and use thereof in the treatment of cancers, but does not disclose its use as a medicament for treating psoriasis. CN104761460A and CN104887652A disclose a compound obtained by modifying glaucocalyxin A at the double bond outside the ring, as well as use thereof in the treatment of tumors and autoimmune diseases. CN1541643A discloses that the glaucocalyxin A can be used to treat autoimmune diseases. However, due to its poor water solubility, small polarity, the long treatment period and large dose required for producing curative effects in the body, fast elimination and short half-life in the body, and low bioavailability, glaucocalyxin A is not suitable for direct administration as a drug.

In addition, although the compound obtained by modifying glaucocalyxin A at the double bond outside the ring as disclosed in CN104761460A and CN104887652A has improved the poor water solubility of glaucocalyxin to a certain extent, such glaucocalyxin A derivatives generally have poor stability, and are liable to be hydrolyzed into glaucocalyxin A in an aqueous solution or plasma, which is then crystallized and precipitated out, seriously affecting their effectiveness and safety, and thus are also not suitable for direct use as an anti-psoriatic drug.

SUMMARY

In view of the deficiencies in the prior art, the present application aims to provide a glaucocalyxin A derivative, and a pharmaceutically acceptable salt thereof, or a pharmaceutical composition comprising the same, and use thereof in the preparation of a medicament for treating psoriasis. To this end, the present application discloses the following technical solutions:

In one aspect, the present application provides use of a glaucocalyxin A derivative, or a pharmaceutically acceptable salt thereof, or a pharmaceutical composition comprising the same, in the preparation of a medicament for treating psoriasis, wherein the glaucocalyxin A derivative is a compound of formula I:

Formula I wherein $R_1$ and $R_2$ are independently hydrogen, amino, substituted or unsubstituted alkyl, substituted or unsubstituted alkenyl, substituted or unsubstituted aryl, or substituted or unsubstituted heteroaryl.

Compared with glaucocalyxin A, the glaucocalyxin A derivative according to the present application has enhanced water solubility and strong effect against psoriasis, thus avoiding the deficiencies of glaucocalyxin A leading to its non-suitability for direct administration as a drug, such as small polarity, poor water solubility, and the large dose and long treatment period required for producing a therapeutic effect in the body. In some embodiments, $R_1$ and $R_2$ are independently hydrogen, amino, methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, benzyl, p-methoxyphenyl, o-methoxyphenyl, 4-chlorophenyl, 3-chlorophenyl, o-chlorophenyl, N-3,4-dichlorophenyl, N-3,5-dichlorophenyl, 2-fluorophenyl, 3-fluorophenyl, 4-fluorophenyl, 2,4-difluorophenyl, 2,3,4-trifluorophenyl, 2-trifluoromethylphenyl, 3-trifluoromethylphenyl, 4-trifluoromethylphenyl, 2-chloro-5-trifluoromethylphenyl, 2-bromo-5-trifluoromethylphenyl, 3,5-bis(trifluoromethyl)phenyl, 2,4,6-trimethylphenyl, 4-propylphenyl, N-p-tolyl, N-methyl-N-phenyl, acetylthio-amino, N-acetyl, 1-naphthyl, 2-phenylethyl, 3,5-dimethyl-1-pyrazolyl, 2-isopropylphenyl, 3-chloro-4-methylphenyl, 2-cyanophenyl, 3-cyanophenyl, 4-cyanophenyl, p-isopropylphenyl, 2-methoxyethyl, 2-morpholinylethyl, 2-furanylmethyl, 2,4,5-triphenyl, 2,4-dimethoxyphenyl, 3,4,5-trimethoxyphenyl, pyridine-3-methyl, 3-morpholinylpropyl, 5-fluoro-2-methylphenyl, 4-iodophenyl, 2-piperidinylethyl, 3-bromophenyl, p-methoxybenzyl, 2,3-dichlorophenyl, 4-trifluoromethoxyphenyl, p-methylbenzyl, 3-methoxybenzyl, 4-phenoxyphenyl, 5-chloro-2-methylphenyl, 2-ethoxyphenyl, 4-hydroxyphenyl, 2,4-dimethoxyphenyl, 2-ethylphenyl, 4-ethylphenyl, p-dimethylaminophenyl, N-decyl, 2,6-diethylphenyl, 4-bromophenyl, 2,4,6-trichlorophenyl, 3-hydroxyphenyl, 3-methoxyphenyl, 2,5-dichlorophenyl, 2-bromophenyl, 2,6-dimethylphenyl, 5-chloro-2-methoxyphenyl, 2,6-dichlorophenyl, 2,5-dimethoxyphenyl, pentafluorophenyl, 4-ethoxyphenyl, 3-phenylpropyl, 2,5-difluorophenyl, 2-methyl-3-chlorophenyl, 3,4-dimethylphenyl, 3-methylphenyl, or 2,5-dimethylphenyl.

In some preferred embodiments, $R_1$ and $R_2$ are independently hydrogen, amino, methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, or benzyl.

In some more preferred embodiments, $R_1$ and $R_2$ are independently hydrogen, amino, methyl, ethyl, n-propyl, isopropyl, n-butyl, n-hexyl, allyl, cyclohexyl, phenyl, or benzyl.

As a preferred embodiment of the present application, the glaucocalyxin A derivative is any one of the following Formulas Ia to Ip, or a combination of at least two thereof:

Formula I a

Formula I b

Formula I c

Formula I d

Formula I e

Formula I f

Formula I g

Formula I h

Formula I i

Formula I j

Formula I k

-continued

Formula I l

Formula I m

Formula I n

Formula I o

Formula I p

Preferably, the pharmaceutically acceptable salt is an organic or inorganic acid salt of the glaucocalyxin A derivative.

Preferably, the organic acid salt is any one selected from the group consisting of tartrate, stearate, oxalate, citrate, lactate, sorbate, fumarate, formate, acetate, benzoate, besylate, ethanesulfonate, resinate, trifluoroacetate, maleate, methanesulfonate, fumarate, amino acid salt, and nicotinate, or a combination of at least two selected therefrom.

Preferably, the inorganic acid salt is any one selected from the group consisting of iodate, phosphate, sulfate, hydroiodide, hydrobromide, nitrate, bromate, and hydrochloride, or a combination of at least two selected therefrom.

Preferably the pharmaceutical composition further comprises a pharmaceutically acceptable auxiliary.

Preferably, the pharmaceutical composition is in the form of an oral preparation, a parenteral preparation, or an external preparation.

In the present application, the psoriasis is selected from the group consisting of psoriasis vulgaris, arthritic psoriasis, pustular psoriasis, and erythrodermic psoriasis. In the present application, the glaucocalyxin A derivative as shown in formula I can be easily obtained by using preparation techniques in the prior art. For example, it may be prepared from glaucocalyxin A and corresponding thiourea compounds according to the preparation method of the thiazolidine derivative of glaucocalyxin A as disclosed in CN104356090A.

In the present application, the glaucocalyxin A derivative can be administered to a mammal, preferably a human in need of treatment for psoriasis, and specifically a therapeutically effective amount of the compound of Formula I, or a pharmaceutically acceptable salt thereof, or a pharmaceutical composition comprising the same, is administered.

Definitions

Unless otherwise indicated, the following terms as used herein shall have the meanings set forth below. A specific term, in the absence of a specific definition, shall be understood according to its common meaning, rather than be considered as uncertain or unclear. The trade name, when referred to herein, is intended to refer to its corresponding commodity or active ingredient(s).

The term "alkyl" refers to a hydrocarbyl group having the general formula $C_nH_{2n+1}$ which may be straight or branched. For example, the term "C1-6 alkyl" refers to an alkyl group containing from 1 to 6 carbon atoms (eg, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl and the like). Similarly, the alkyl moiety (i.e., alkyl) of an alkoxy group, an alkylamino group, a dialkylamino group, an alkylsulfonyl group, and an alkylthio group has the same definition as defined above.

The term "alkenyl" refers to a straight- or branched-chain unsaturated aliphatic hydrocarbon group consisting of carbon atoms and hydrogen atoms having at least one double bond. Non-limiting examples of alkenyl groups include, but are not limited to, ethenyl, 1-propenyl, 2-propenyl, 1-butenyl, isobutenyl, or 1,3-butadienyl, and the like.

The term "aryl" refers to an all-carbon monocyclic or fused polycyclic aromatic ring group having a conjugated n-electron system. For example, an aryl group can have from 6 to 20 carbon atoms, from 6 to 14 carbon atoms, or from 6 to 12 carbon atoms. Non-limiting examples of aryl groups include, but are not limited to, phenyl, naphthyl, anthranyl, 1,2,3,4-tetrahydronaphthalene, and the like.

The terms "treat," "treating," or "treatment" means administration of the compound or formulation according to the present application to prevent, ameliorate, or eradicate a disease or one or more symptoms associated with the disease, including:

(i) preventing the disease or condition from occurring in a mammal, especially when such mammal is predisposed to the condition but has not yet been diagnosed as having it;

(ii) inhibiting the disease or condition, i.e., arresting its development;

(iii) relieving the disease or condition, i.e., causing regression of the disease or condition.

The term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications, commensurate with a reasonable benefit/risk ratio.

As a pharmaceutically acceptable salt, for example, a metal salt, an ammonium salt, a salt with an organic base, a salt with an inorganic acid, a salt with an organic acid, a salt with a basic or acidic amino acid, or the like may be mentioned. The inorganic acid is selected from the group consisting of iodic acid, phosphoric acid, sulfuric acid, hydroiodic acid, hydrobromic acid, nitric acid, bromic acid, and hydrochloric acid. The organic acid is selected from the group consisting of tartaric acid, stearic acid, oxalic acid, citric acid, lactic acid, sorbic acid, fumaric acid, formic acid, acetic acid, benzoic acid, benzenesulfonic acid, ethanesulfonic acid, resin acid, trifluoroacetic acid, maleic acid, methanesulfonic acid, fumaric acid, amino acid, and niacin.

The term "pharmaceutical composition" refers to a mixture of one or more compounds of the present application or a salt thereof and a pharmaceutically acceptable auxiliary. The purpose of a pharmaceutical composition is to facilitate administration of the compound of the present application to an organism.

The term "pharmaceutically acceptable auxiliary" refers to those that do not cause significant irritation to an organism and do not abrogate the biological activity and properties of the active compound. Suitable auxiliaries are well known to those skilled in the art, such as carbohydrates, waxes, water-soluble and/or water-swellable polymers, hydrophilic or hydrophobic materials, gelatin, oils, solvents, water, and the like.

The pharmaceutical composition of the present application may be prepared by combining the compound of the present application with a suitable pharmaceutically acceptable auxiliary, and for example, may be formulated into preparations in solid, semi-solid, liquid, or gaseous forms, such as tablets, pills, capsules, powders, granules, ointments, emulsions, suspensions, suppositories, injections, inhalants, gels, microspheres, and aerosols.

Typical routes of administration of the compound of the present application, or a pharmaceutically acceptable salt thereof, or a pharmaceutical composition comprising the same include, but are not limited to, oral, rectal, topical, inhalation, parenteral, sublingual, intravaginal, intranasal, intraocular, intraperitoneal, intramuscular, subcutaneous, and intravenous administration.

The pharmaceutical composition of the present application may be manufactured by processes well known in the art, e.g., by means of conventional mixing, dissolving, granulating, dragee-making, levigating, emulsifying, or lyophilizing processes, and the like.

In some embodiments, the pharmaceutical composition is in the form of an oral formulation. For oral administration, the pharmaceutical composition can be formulated by mixing the active compound with pharmaceutically acceptable auxiliaries well known in the art. Such auxiliaries enable the compound of the present application to be formulated as tablets, pills, lozenges, dragees, capsules, liquids, gels, syrups, suspensions and the like, for oral administration to a patient.

The solid oral compositions may be prepared by conventional methods of blending, filling, or tabletting. For example, they may be obtained by the following processes: mixing the active compound with solid auxiliaries, optionally grinding the resulting mixture, and adding other suitable auxiliaries, if desired, followed by processing the mixture into granules to obtain tablets or dragee cores. Suitable auxiliaries include, but are not limited to, binders, diluents, disintegrants, lubricants, glidants, sweeteners, or flavoring agents, and the like.

The pharmaceutical compositions may also be in the form of a parenteral preparation such as a sterile solution, suspension, or lyophilized product in a suitable unit dosage form.

The compounds of the present application may be prepared by various synthetic methods well known to those skilled in the art, including the specific embodiments set forth below, a combination thereof with other chemical synthetic methods and equivalent alternative methods well known to those skilled in the art. The preferred embodiments include, but are not limited to, the examples of the present application.

The chemical reactions in the specific embodiments of the present application are carried out in a suitable solvent which is suitable for the chemical changes of the present application and the reagents and materials required therefor. In order to obtain the compounds of the present application, it is sometimes necessary for those skilled in the art to modify or select the synthetic steps or reaction schemes based on the existing embodiments.

The glaucocalyxin A derivatives, and pharmaceutically acceptable salts thereof, and pharmaceutical compositions of the present application have a strong activity of inhibiting the proliferation of human skin keratinocytes, that is, they have an activity against psoriasis.

In another aspect, the present application provides a glaucocalyxin A derivative that has the structure of formula I':

Formula I' wherein $R_1$ and $R_2$ are independently amino, substituted or unsubstituted alkyl, substituted or unsubstituted alkenyl, substituted or unsubstituted aryl, or substituted or unsubstituted heteroaryl.

The glaucocalyxin A derivatives or salts thereof of the present application have good water solubility, thus overcoming the druggability problem caused by the poor water solubility of glaucocalyxin A. In addition, it is found for the first time that they have good effects in the treatment of psoriasis. On the other hand, the glaucocalyxin A derivative as shown in Formula I', which is bi-substituted on the nitrogen atom at the side chain of the heterocycle, has an enhanced activity and improved safety, thus overcoming the deficiencies of the compound reported in CN104356090A when applied in the treatment of this indication (psoriasis), such as poor stability and liability to be hydrolyzed into glaucocalyxin A in an aqueous solution or plasma, which is then crystallized and precipitated out, seriously affecting their effectiveness and safety.

In the present application, the glaucocalyxin A derivatives which are bi-substituted with $R_1$ and $R_2$ on the nitrogen atom have superior effects in the treatment of psoriasis, including better pharmacological activity and better safety, as compared to the glaucocalyxin A derivatives which are mono- or unsubstituted on the nitrogen atom.

In some preferred embodiments, $R_1$ and $R_2$ are independently methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, or benzyl.

In some preferred embodiments, the glaucocalyxin A derivative has any one of the following formulas If, In, Io, or Ip:

Formula If

Formula In

Formula Io

Formula Ip

In another aspect, the present application provides a method for preparing the glaucocalyxin A derivative as described above, comprising reacting 2-bromoglaucocalyxin A with N,N-dialkylthiourea to provide a glaucocalyxin A derivative of formula I'.

In the present application, the reaction equation of the reaction is as follows:

wherein $R_1$ and $R_2$ are independently amino, substituted or unsubstituted alkyl, substituted or unsubstituted alkenyl, substituted or unsubstituted aryl, or substituted or unsubstituted heteroaryl;

preferably, $R_1$ and $R_2$ are independently methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, or benzyl.

More preferably, $R_1$ and $R_2$ are independently methyl, ethyl, n-propyl, or isopropyl.

Compared with the prior art, the present application has the following beneficial effects:

The glaucocalyxin A derivatives, and pharmaceutically acceptable salts thereof, and pharmaceutical compositions comprising the same according to the present application can effectively inhibit the proliferation of keratinocytes, inhibit the inflammatory response in keratinocytes caused by γ-interferon, and inhibit acute inflammation in mice, with good safety and tolerance. The glaucocalyxin A derivatives, and pharmaceutically acceptable salts thereof, and pharmaceutical compositions comprising the same according to the present application can be used as drugs or pro-drugs for treating psoriasis.

In the present application, the glaucocalyxin A derivatives which are bi-substituted with $R_1$ and $R_2$ on the nitrogen atom have superior effects in the treatment of psoriasis, including better pharmacological activity and better safety, as compared to the glaucocalyxin A derivatives which are mono- or unsubstituted on the nitrogen atom.

DETAILED DESCRIPTION

The technical solutions of the present application are further described below by way of illustrating specific embodiments. It should be understood by those skilled in the art that the examples are only described to help understand the present application and should not be considered as a limitation of the present application.

Example 1 (Preparation of a Hydrobromide Salt of the Compound of Formula If)

Step 1: Preparation of 2-bromoglaucocalyxin A

PyBr$_3$ (96.22 mg, 0.30 mmol) was added to a solution of glaucocalyxin A (100 mg, 0.30 mmol) in DMF (4 ml) at room temperature. The reaction mixture was stirred at room temperature for 5 h, then poured into water, suction-filtered, and dried to give a mixture of two epimers as a white solid (106.33 mg, yield 86.1%), which was directly used for the next reaction without separation. MS ESI-MS m/z 412 [H$^+$].

Step 2: Preparation of a Hydrobromide Salt of the Compound of Formula If

N,N-Dimethylthiourea (12.66 mg, 0.12 mmol) was' added to a solution of 2-bromoglaucocalyxin A (50 mg, 0.12 mmol) in ethanol (4 ml) at room temperature. The reaction mixture was heated under reflux for 3 h. The mixture was slowly cooled down, and a solid was precipitated, suction-filtered, and dried to give a white solid powder (Compound 23, 40.54 mg, yield 67.91%). MS ESI-MS nm/z 417 [H$^+$].

Example 2 (Preparation of a Hydrobromide Salt of the Compound of Formula In)

N,N-Diethylthiourea (15.87 mg, 0.12 mmol) was added to a solution of 2-bromoglaucocalyxin A (50 mg, 0.12 mmol) in ethanol (4 ml) at room temperature. The reaction mixture was heated under reflux for 3 h. The mixture was slowly cooled down, and a solid was precipitated, suction-filtered, and dried to give a white solid powder (38.23 mg, yield 60.62%). MS ESI-MS m/z 445 [H$^+$].

Example 3 (Preparation of a Hydrobromide-Salt of the Compound of Formula Io)

N,N-Dipropylthiourea (19.23 mg, 0.12 mmol) was added to a solution of 2-bromoglaucocalyxin A (50 mg, 0.12 mmol) in ethanol (4 ml) at room temperature. The reaction mixture was heated under reflux for 3 h. The mixture was slowly cooled down, and a solid was precipitated, suction-filtered, and dried to give a white solid powder (35.48 mg, yield 53.41%). MS ESI-MS m/z 473 [H⁺].

Example 4 (Preparation of a Hydrobromide Salt of the Compound of Formula Ip)

N,N-Diisopropylthiourea (19.23 mg, 0.12 mmol) was added to a solution of 2-bromoglaucocalyxin A (50 mg, 0.12 mmol) in ethanol (4 ml) at room temperature. The reaction mixture was heated under reflux for 3 h. The mixture was slowly cooled down, and a solid was precipitated, suction-filtered, and dried to give a white solid powder (30.17 mg, yield 45.41%). MS ESI-MS m/z 473 [H⁺].

Example 5

In this example, the glaucocalyxin A derivatives of the present application, or pharmaceutically acceptable salts thereof, were examined for the effect on the proliferation of human keratinocytes. In this example, the glaucocalyxin A derivatives as shown in Table 1 were examined by using the following procedure.

A cell suspension was prepared and inoculated into three 96-well plates at 8000 cells in a volume of 150 µl per well, which were then cultured overnight in an incubator at 37° C., 5% $CO_2$. On the next day, 50 µl of test compound solution at different concentrations was added to each well. Triplicate wells were set up for each concentration. A vehicle control group (without compound), a cell control group (without compound and vehicle), and a blank medium control group (without cells, a well for null adjustment) were also set up, and cultured for an additional 48 hours. CCK-8 staining working solution was added at 110 µL per well, and cultured for additional 1-4 h. At the end of the culture, the absorbances were measured at 450 nm (OD450 nm) on a Bio-Tek enzyme-linked immunosorbent assay. The results were expressed as the mean OD450 nm value of triplicates±standard deviation ($\bar{x}$±sd). The Origin 7.0 was used for plotting and analysis. A fitting curve was obtained by plotting the OD value of each group against the logarithmic concentration of the test compound, and then the $IC_{50}$ value was determined.

It can be seen from the $IC_{50}$ values in Table 1 that within the range of concentrations tested, the glaucocalyxin A derivatives and salts thereof significantly affected the growth and survival of the cultured human keratinocytes (HaCaT) after 48 hours of treatment, suggesting that the glaucocalyxin A derivatives had a significant dose-dependent inhibitory effect on the proliferation of human epidermal keratinocytes. The $IC_{50}$ value of each compound was shown in Table 1. It can be seen that the glaucocalyxin A derivatives (Formula I) had an anti-psoriatic activity with an $IC_{50}$ of about 1-10 µM, indicating a low effective dose. It can be seen from the data in Table 1 that when both $R_1$ and $R_2$ in Formula I were substituted, the pharmacological activity of the compound was generally enhanced, and superior to the glaucocalyxin A derivative reported in CN104356090A which was mono-substituted or unsubstituted on the nitrogen atom. Among them, Compound 23 was the most effective one.

TABLE 1

| Comp. No. | General formula | R group | Molecular formula | MW | IC50 (µM, 48 h) |
|---|---|---|---|---|---|
| 01 | a hydrochloride salt of Formula I | $R_1$ and $R_2$ are both H | $C_{21}H_{28}N_2O_3S \cdot HCl$ | 424.98 | 3.21 |
| 02 | an acetate salt of Formula I | $R_1$ and $R_2$ are both H | $C_{21}H_{28}N_2O_3S \cdot C_2H_4O_2$ | 448.57 | 3.52 |
| 03 | a maleic acid salt of Formula I | $R_1$ and $R_2$ are both H | $C_{21}H_{28}N_2O_3S \cdot C_4H_4O_4$ | 504.59 | 4.02 |
| 04 | a fumarate salt of Formula I | $R_1$ and $R_2$ are both H | $C_{21}H_{28}N_2O_3S \cdot C_4H_4O_4$ | 504.59 | 4.10 |
| 05 | a sulfate salt of Formula I | $R_1$ and $R_2$ are both H | $C_{21}H_{28}N_2O_3S \cdot H_2SO_4$ | 486.60 | 3.45 |
| 06 | a phosphate salt of Formula I | $R_1$ and $R_2$ are both H | $C_{21}H_{28}N_2O_3S \cdot H_3PO_4$ | 486.52 | 2.91 |
| 07 | a nitrate salt of Formula I | $R_1$ and $R_2$ are both H | $C_{21}H_{28}N_2O_3S \cdot HNO_3$ | 451.52 | 3.28 |
| 08 | a hydrobromide salt of Formula I | $R_1$ and $R_2$ are both H | $C_{21}H_{28}N_2O_3S \cdot HBr$ | 469.50 | 2.85 |
| 09 | a citrate salt of Formula I | $R_1$ and $R_2$ are both H | $C_{21}H_{28}N_2O_3S \cdot C_6H_8O_7$ | 580.66 | 2.42 |
| 10 | a tartrate salt of Formula I | $R_1$ and $R_2$ are both H | $C_{21}H_{28}N_2O_3S \cdot C_4H_6O_6$ | 538.61 | 3.86 |
| 11 | a methanesulfonate salt of Formula I | $R_1$ and $R_2$ are both H | $C_{21}H_{28}N_2O_3S \cdot CH_4O_3S$ | 484.62 | 3.00 |
| 12 | a hydrobromide salt of Formula I | $R_1$ is amino and $R_2$ is H | $C_{21}H_{29}N_3O_3S \cdot HBr$ | 484.45 | 1.21 |

TABLE 1-continued

| | | | | | |
|---|---|---|---|---|---|
| 13 | a hydrobromide salt of Formula I | $R_1$ is 4-pyridyl and $R_2$ is H | $C_{26}H_{31}N_3O_3S \cdot HBr$ | 546.52 | 3.62 |
| 14 | a hydrobromide salt of Formula I | $R_1$ is n-propyl and $R_2$ is H | $C_{24}H_{34}N_2O_3S \cdot HBr$ | 511.52 | 7.00 |
| 15 | a hydrobromide salt of Formula I | $R_1$ is isopropyl and $R_2$ is H | $C_{24}H_{34}N_2O_3S \cdot HBr$ | 511.52 | 6.95 |
| 16 | a hydrobromide salt of Formula I | $R_1$ is n-butyl and $R_2$ is H | $C_{25}H_{36}N_2O_3S \cdot HBr$ | 525.55 | 8.88 |
| 17 | a hydrobromide salt of Formula I | $R_1$ is n-hexyl and $R_2$ is H | $C_{27}H_{40}N_2O_3S \cdot HBr$ | 553.60 | 4.29 |
| 18 | a hydrobromide salt of Formula I | $R_1$ is allyl and $R_2$ is H | $C_{24}H_{32}N_2O_3S \cdot HBr$ | 509.50 | 7.24 |
| 19 | a hydrobromide salt of Formula I | $R_1$ is cyclohexyl and $R_2$ is H | $C_{27}H_{38}N_2O_3S \cdot HBr$ | 551.58 | 8.16 |
| 20 | a hydrobromide salt of Formula I | $R_1$ is Phenyl and $R_2$ is H | $C_{27}H_{32}N_2O_3S \cdot HBr$ | 545.54 | 9.31 |
| 21 | a hydrobromide salt of Formula I | $R_1$ is Benzyl and $R_2$ is H | $C_{28}H_{34}N_2O_3S \cdot HBr$ | 559.56 | 9.20 |
| 22 | Formula If | $R_1$ is methyl and $R_2$ is methyl | $C_{23}H_{32}N_2O_3S \cdot HBr$ | 416.58 | 0.95 |
| 23 | a hydrobromide salt of Formula If | $R_1$ is methyl and $R_2$ is methyl | $C_{23}H_{33}BrN_2O_3S \cdot HBr$ | 497.49 | 0.93 |
| 24 | a hydrobromide salt of Formula I | $R_1$ is methyl and $R_2$ is H | $C_{22}H_{30}N_2O_3S \cdot HBr$ | 483.47 | 3.17 |
| 25 | a hydrobromide salt of Formula I | $R_1$ is ethyl and $R_2$ is H | $C_{23}H_{32}N_2O_3S \cdot HBr$ | 497.49 | 5.49 |
| 26 | a hydrobromide salt of Formula I | $R_1$ is propyl and $R_2$ is H | $C_{24}H_{34}N_2O_3S \cdot HBr$ | 511.52 | 7.86 |
| 27 | a hydrobromide salt of Formula I | $R_1$ is isopropyl and $R_2$ is H | $C_{24}H_{34}N_2O_3S \cdot HBr$ | 511.52 | 6.92 |
| 28 | a hydrobromide salt of Formula In | $R_1$ is ethyl and $R_2$ is ethyl | $C_{25}H_{36}N_2O_3S \cdot HBr$ | 525.55 | 1.26 |
| 29 | a hydrobromide salt of Formula Io | $R_1$ is propyl and $R_2$ is propyl | $C_{27}H_{40}N_2O_3S \cdot HBr$ | 553.60 | 1.85 |
| 30 | a hydrobromide salt of Formula Ip | $R_1$ is isopropyl and $R_2$ is isopropyl | $C_{27}H_{40}N_2O_3S \cdot HBr$ | 553.60 | 2.37 |
| 31 | glaucocalyxin A | | $C_{20}H_{28}O_4$ | 332.43 | 30.46 |
| 32 | dimethylamino glaucocalyxin A hydrochloride as disclosed in CN104761460A | | $C_{22}H_{36}ClNO_4$ | 413.98 | 18.74 |

The glaucocalyxin A denoted as Compound 31 had the structure of which is disclosed, for example, as the "wangzaozi ne B" in CN1541643A. The dimethylamino glaucocalyxin A hydrochloride as disclosed in CN104761460A denoted as Compound 32 had the structure of Example 6

In this example, the glaucocalyxin A derivatives of the present application and pharmaceutically acceptable salts thereof were examined for the relationship between the inhibitory rate thereof on the proliferation of human keratinocytes and its concentration. Compound 23 as shown in Table 1 was used as an exemplary compound to be examined by using the following procedure.

A cell suspension was prepared and inoculated into three 96-well plates at 8000 cells in a volume of 150 μl per well, which were then cultured overnight in an incubator at 37° C., 5% $CO_2$. On the next day, 50 μl of test compound solution at different concentrations was added to each well. Triplicate wells were set up for each concentration. A vehicle control group (without compound), a cell control group (without compound and without vehicle), and a blank medium control group (without cells, a well for null adjustment) were also set up, and cultured for additional 24, 48, and 72 hours. CCK-8 staining working solution was added at 110 μL per well, and cultured for additional 1-4 h. At the end of the culture, the absorbances were measured at 450 nm (OD450 nm) on a Bio-Tek enzyme-linked immunosorbent assay. The results were expressed as the mean OD450 nm value of the triplicates±standard deviation ($\bar{x}$±sd). Prism Graph was used for plotting and analysis. The cell inhibitory rate of each group was calculated according to the mean value of the treatment group with each compound at each concentration and the mean value of the vehicle control group, that is, the cell inhibitory rate (%)=[1−(the mean value of the treatment group−the blank control group)/(the mean value of the vehicle control group−the blank control group)]×100%. A fitting curve was obtained by plotting the cell inhibitory rate of each group against the logarithmic concentration (Log C) of the test compound, and then the $IC_{50}$ value was determined.

Figure 1:
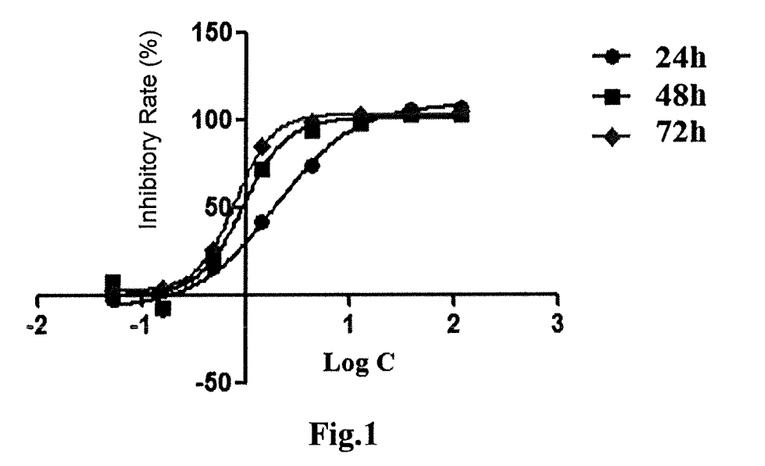
FIG. 1 is a graph showing the time- and dose-dependent effect of the hydrobromide of the compound of Formula If (Compound 23) on the proliferation of human keratinocytes.

The measurement results of Compound 23 were shown in FIG. 1, from which it can be seen that within the range of concentrations tested, Compound 23 significantly affected the growth and survival of the cultured HaCaT keratinocytes after 24, 48, and 72 hours of treatment. Compound 23 inhibited the proliferation of HaCaT cells in a dose- and time-effect relationship, suggesting that Compound 23 had a significant dose-dependent inhibitory effect on the proliferation of human epidermal keratinocytes, wherein the inhibitory effect was enhanced as the drug action time prolonged. It can be seen from FIG. 1 that the $IC_{50}$ values of Compound 23 at 24 h, 48 h and 72 h were 1.935, 0.933, and 0.787 μM, respectively.

Example 7

In this example, the glaucocalyxin A derivatives and pharmaceutically acceptable salts thereof were detected for the inhibitory effect thereof on xylene-induced auricular swelling in mice. Compound 23 was used as an exemplary compound, and the detection method was as follows.

20 mice were randomly divided into 4 groups with 5 mice in each group, which were blank control group, 30 mg/kg dexamethasone treatment group, Compound 23 (10 mg/kg) treatment group, and Compound 23 (50 mg/kg) treatment group, respectively. 0.25-0.3 mL depending on the body weight was intragastrically administrated for 7 consecutive days, and an equal volume of 5% glucose injection was administrated to the blank group. On the 8th day, xylene was used to produce a model of auricular swelling in the right auricle of mice. 15 μl of xylene, an inflammatory inducer, was applied to both sides of the right auricle of each mouse, and the left auricle was left un-treated as a normal auricle control. After 1 hour, the mice were sacrificed by cervical dislocation. Both auricles were cut off along the auricle baseline, and then punched at the same position by using a puncher with a diameter of 8 mm to give auricle pieces, which were then weighed on an electronic analytical balance. The auricular swelling rate and the auricular swelling inhibitory rate were calculated according to the following formula. Swelling rate (%)=(weight of the auricle piece from the inflammatory side−weight of the auricle piece from the non-inflammatory side)/weight of the auricle piece from the non-inflammatory side×100%; swelling inhibitory rate (%)=(average swelling degree of the model group−average swelling degree of the administration group)/average swelling degree of the model group×100%.

Figure 2:
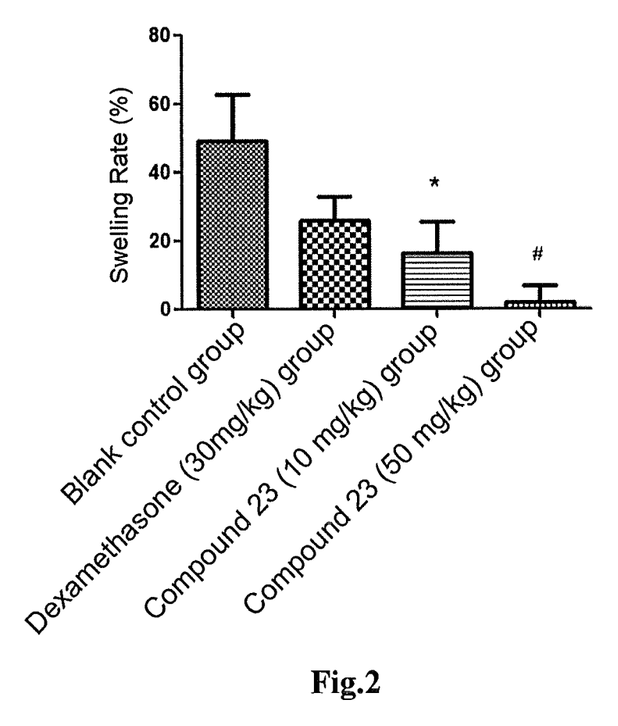
FIG. 2 is a graph showing the inhibitory effect of the hydrobromide of the compound of Formula If (Compound 23) on xylene-induced auricular swelling in mice; wherein the abscissa represents the grouping, comprising blank control group, dexamethasone (30 mg/kg) treatment group, Compound 23 (10 mg/kg) treatment group, and Compound 23 (50 mg/kg) treatment group sequentially from left to right.

The inhibitory rate of Compound 23 against xylene-induced auricular swelling in mice was shown in FIG. 2. It can be seen from FIG. 2 that both 10 mg/kg of Compound 23 and 50 mg/kg of Compound 23 were effective for inhibiting the auricular swelling in mice, indicating that compound 23 had an acute anti-inflammatory effect.

Example 8

In this example, the glaucocalyxin A derivatives and pharmaceutically acceptable salts thereof were detected for the effect thereof on ConA-induced proliferation of mouse spleen lymphocytes. Compound 23 was used as an exemplary compound, and the detection method was as follows $2\times10^7$/mL cell suspension was prepared and a 5 μg/μL ConA stock solution was added thereto at a final concentration of 5 μg/mL. The resulting mixture was inoculated into a 96-well culture plate at 0.1 mL per well. Then 0.1 mL of test compound at different concentrations was added to each well. Triplicate or quadruplicate wells were set up for each group, and a vehicle control group (without compound), a stimulant control group (with ConA, without compound, and without vehicle), a cell control group (without ConA, without compound, and without vehicle), and a blank medium control group (without cells, a well for null adjustment) were also set up, and cultured at 37° C., 5% $CO_2$ for 48 h. MTT solution at 5 mg/mL was added at 20 μl per well, and cultured for an additional 4 hours. The culture plate was taken out and centrifuged at 1000 rpm for 10 min. The supernatant of each well was aspirated, and 100 μL of SDS cell lysis solution was added to each well, and cultured overnight. On the next day, the absorbance at 550 nm ($OD_{550nm}$) was measured on an enzyme-linked immunoassay analyzer. The results were expressed as the mean $OD_{550nm}$ value of the triplicates or quadruplicates±standard deviation ($\bar{x}\pm sd$). SPSS software version 17.0 was used for statistical analysis of the mean values, that is, the vehicle group was compared with the stimulant group, and the test group of each compound concentration was compared with the corresponding vehicle control group. The cell survival rate of each group was calculated according to the mean value for the compound treatment group and the mean value for the vehicle control group, that is, the cell survival rate (%)=the mean value for the compound treatment group/the mean value for the vehicle control group×100%. A linear regression equation was obtained by plotting the cell survival rate of each group against the concentration of the test compound, statistical test of the correlation coefficient was conducted, and then the $IC_{50}$ value was determined.

The results of the effect of treatment with Compound 23 for 48 hours on 5 μg/mL ConA-induced proliferation of mouse spleen lymphocytes were shown in Table 2. The results of the effect of treatment with cyclosporin A for 48 hours on 5 μg/mL ConA-induced proliferation of mouse spleen lymphocytes were shown in Table 3. The results of the effect of treatment with triptolide for 48 hours on 5 μg/mL ConA-induced proliferation of mouse spleen lymphocytes were shown in Table 4. As can be seen from the data in Tables 2-4, within the range of concentrations tested, Compound 23 had a significant effect on 5 μg/mL ConA-induced proliferation of mouse spleen lymphocytes after 48 hours of treatment, and had an $IC_{50}$ value of about 9.41 μM. The control drugs cyclosporine A and triptolide also showed varying degrees of inhibition at different tested concentrations.

TABLE 2

| Concentration (μg/mL) | Number of samples (n) | $OD_{550nm}$ value ($\bar{x} \pm sd$) | Survival rate (%) | Linear regression equation and $IC_{50}$ (μg/mL) |
|---|---|---|---|---|
| 100 | 4 | 0.02 ± 0.02**## | 1 | y = −48.524 Logx + |
| 50 | 4 | 0.02 ± 0.01**## | 2 | 79.226 |
| 25 | 4 | 0.02 ± 0.01**## | 2 | r = 0.8554 |
| 12.5 | 4 | 0.07 ± 0.02**## | 6 | n = 7, $p_2 < 0.05$ |
| 6.25 | 4 | 0.29 ± 0.03**## | 25 | $IC_{50}$ = 4.00 |
| 3.125 | 4 | 0.52 ± 0.04**## | 45 | (9.41 μM) |
| 1.5625 | 4 | 1.18 ± 0.16 | 101 | |
| 0.78125 | 4 | 1.14 ± 0.11 | 98 | |

TABLE 2-continued

| Concentration (µg/mL) | Number of samples (n) | OD$_{550nm}$ value ($\bar{x} \pm sd$) | Survival rate (%) | Linear regression equation and IC$_{50}$ (µg/mL) |
|---|---|---|---|---|
| DMSO vehicle group (5‰) | 4 | 1.16 ± 0.02 | — | |
| Stimulant control group | 4 | 1.14 ± 0.07 | — | |
| Cell control group | 4 | 0.54 ± 0.03 | — | |

Note:
(1) Compared with the stimulant control group, *<0.05; **<0.01
(2) Compared with the vehicle group, #<0.05; ##<0.01

TABLE 3

| Concentration (µg/mL) | Number of samples (n) | OD$_{550nm}$ value ($\bar{x} \pm sd$) | Survival rate (%) |
|---|---|---|---|
| 10 | 4 | 0.40 ± 0.02**## | 39 |
| 0.1 | 4 | 0.48 ± 0.03**## | 47 |
| Ethanol vehicle group (1‰) | 3 | 1.03 ± 0.11 | — |
| Stimulant control group | 4 | 0.90 ± 0.07 | — |
| Cell control group | 4 | 0.53 ± 0.07 | — |

Note:
(1) Compared with the stimulant control group, *<0.05; **<0.01
(2) Compared with the vehicle group, #<0.05; ##<0.01

TABLE 4

| Concentration (µg/mL) | Number of samples (n) | OD$_{550nm}$ value ($\bar{x} \pm sd$) | Survival rate (%) |
|---|---|---|---|
| 0.1 | 4 | 0.42 ± 0.03**## | 40 |
| 0.001 | 4 | 1.03 ± 0.10 | 98 |
| DMSO vehicle group (0.01‰) | 3 | 1.05 ± 0.11 | — |
| Stimulant control group | 4 | 0.90 ± 0.07 | — |
| Cell control group | 4 | 0.53 ± 0.07 | — |

Note:
(1) Compared with the stimulant control group, *<0.05; **<0.01
(2) Compared with the vehicle group, #<0.05; ##<0.01

Example 9

In this example, Compound 23 and Compound 24 were detected for their acute toxicities, and the detection method was as follows.

Experimental procedure: 40 BALB/c mice, half male and half female, were randomly divided into groups after weight measurement. The weight of an individual should be within the range of the average body weight±20%. Animals should be allowed to acclimatize to the environment for at least 5 days before the test, and healthy (if female, it must be un-pregnant) mice were selected as test animals. The main inspections during the acclimatization period included: whether it met the quality indicators required at the time of ordering; general state check; and whether the weight reached the weight range required by the test. Unqualified abnormal animals were not included in this test. A single tail-vein injection was administrated to the mice at a low, medium, or high dose, which was 5 mg/kg, 10 mg/kg or 40 mg/kg respectively according to a blank preparation pre-test. An equal volume of vehicle was intravenously injected to establish a control group.

Observation method: (1) General state observation: Animals were observed for conditions including, but not limited to, appearance signs, administration sites (with or without bleeding, redness, purpura, induration, suppuration, or ulceration), hair coat, general behavior, mental state, gland secretion, color of skin and mucosa, respiratory state, fecal traits, genitals, and death, and other toxic symptoms. Mice were observed once respectively at 0 to 2 hours and 4 to 6 hours after each administration. If toxic symptoms occurred, the number of observations could be increased. (2) Gross anatomy observation: All the surviving mice in each group were dissected and observed on the 8th day of the experiment. The abnormal organs and tissues found in the observation of administration sites and in the gross anatomy observation that might be related to the test samples were photographed and recorded. (3) Disposal of dying animals: The state of the mouse and the observation time were recorded, and the body weight was measured. (4) Disposal of dead animals: The time of death or the time when the death was found was recorded, the body weight was measured, and then the dissection was quickly performed for gross observation to speculate the cause of death.

Experimental results: No obvious toxic side effects were observed, and no significant weight loss and decreased diet were found in BALB/c mice treated with a single intravenous injection of Compound 23 (5 mg/kg, 10 mg/kg, or 40 mg/kg). All animals treated with a single intravenous injection of Compound 24 (10 mg/kg) died. The above results indicated that Compound 23 is safer than Compound 24.

The applicant states that although the glaucocalyxin A derivatives, or pharmaceutically acceptable salts thereof, or pharmaceutical compositions comprising the same according to the present application, and their use in the preparation of a medicament for treating psoriasis are illustrated herein through the above embodiments, the present application is not limited to the above embodiments, and it does not mean that the present application must rely on the above embodiments to implement. It should be apparent to those skilled in the art that, for any improvement of the present application, the equivalent replacement of the raw materials selected in the present application, the addition of auxiliary components, and the selection of specific modes, etc., will all fall within the protection scope and the disclosure scope of the present application.

The invention claimed is:

1. A method for treating psoriasis, comprising administrating a therapeutically effective amount of a glaucocalyxin A derivative, or a pharmaceutically acceptable salt thereof, or a pharmaceutical composition comprising the glaucocalyxin A derivative or the pharmaceutically acceptable salt thereof to a subject in need thereof, wherein the glaucocalyxin A derivative is a compound of formula I:

Formula I wherein R₁ and R₂ are independently hydrogen, amino, cyclohexyl, alkyl, alkenyl, aryl, or heteroaryl.

2. The method according to claim 1, wherein R₁ and R₂ are independently hydrogen, amino, methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, benzyl, p-methoxyphenyl, o-methoxyphenyl, 4-chlorophenyl, 3-chlorophenyl, o-chlorophenyl, N-3,4-dichlorophenyl, N-3,5-dichlorophenyl, 2-fluorophenyl, 3-fluorophenyl, 4-fluorophenyl, 2,4-difluorophenyl, 2,3,4-trifluorophenyl, 2-trifluoromethylphenyl, 3-trifluoromethylphenyl, 4-trifluoromethyl phenyl, 2-chloro-5-trifluoromethyl phenyl, 2-bromo-5-trifluoromethylphenyl, 3,5-bis(trifluoromethyl)phenyl, 2,4,6-trimethylphenyl, 4-propylphenyl, N-p-tolyl, N-methyl-N-phenyl, acetylthioamino, N-acetyl, 1-naphthyl, 2-phenylethyl, 3,5-dimethyl-1-pyrazolyl, 2-isopropylphenyl, 3-chloro-4-methylphenyl, 2-cyanophenyl, 3-cyanophenyl, 4-cyanophenyl, p-isopropylphenyl, 2-methoxyethyl, 2-morpholinylethyl, 2-furanylmethyl, 2,4,5-triphenyl, 2,4-dimethoxyphenyl, 3,4,5-trimethoxyphenyl, pyridine-3-methyl, 3-morpholinylpropyl, 5-fluoro-2-methylphenyl, 4-iodophenyl, 2-piperidinylethyl, 3-bromophenyl, p-methoxybenzyl, 2,3-dichlorophenyl, 4-trifluoromethoxyphenyl, p-methylbenzyl, 3-methoxybenzyl, 4-phenoxyphenyl, 5-chloro-2-methylphenyl, 2-ethoxyphenyl, 4-hydroxyphenyl, 2,4-dimethoxyphenyl, 2-ethylphenyl, 4-ethylphenyl, p-dimethylaminophenyl, N-decyl, 2,6-diethylphenyl, 4-bromophenyl, 2,4,6-trichlorophenyl, 3-hydroxyphenyl, 3-methoxyphenyl, 2,5-dichlorophenyl, 2-bromophenyl, 2,6-dimethylphenyl, 5-chloro-2-methoxyphenyl, 2,6-dichlorophenyl, 2,5-dimethoxyphenyl, pentafluorophenyl, 4-ethoxyphenyl, 3-phenylpropyl, 2,5-difluorophenyl, 2-methyl-3-chlorophenyl, 3,4-dimethylphenyl, 3-methylphenyl, or 2,5-dimethylphenyl.

3. The method according to claim 1, wherein R₁ and R₂ are independently hydrogen, amino, methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, or benzyl.

4. The method according to claim 1, wherein R₁ and R₂ are independently hydrogen, amino, methyl, ethyl, n-propyl, isopropyl, n-butyl, n-hexyl, allyl, cyclohexyl, phenyl, or benzyl.

5. The method according to claim 1, wherein the glaucocalyxin A derivative is any one of the following Formulas Ia to Ip, or a combination of at least two thereof:

Formula I a

Formula I b

Formula I c

Formula I d

Formula I e

Formula I f

Formula I g

Formula I h

Formula I i

-continued

Formula I j

Formula I k

Formula I l

Formula I m

Formula I n

Formula I o

Formula I p

6. The method according to claim 1, wherein the pharmaceutically acceptable salt is an organic or inorganic acid salt of the glaucocalyxin A derivative.

7. The method according to claim 6, wherein the organic acid salt is any one selected from the group consisting of tartrate, stearate, oxalate, citrate, lactate, sorbate, fumarate, formate, acetate, benzoate, besylate, ethanesulfonate, resinate, trifluoroacetate, maleate, methanesulfonate, fumarate, amino acid salt, and nicotinate, or a combination of at least two selected therefrom.

8. The method according to claim 6, wherein the inorganic acid salt is any one selected from the group consisting of iodate, phosphate, sulfate, hydroiodide, hydrobromide, nitrate, bromate, and hydrochloride, or a combination of at least two selected therefrom.

9. The method according to claim 1, wherein the pharmaceutical composition further comprises a pharmaceutically acceptable auxiliary.

10. The method according to claim 9, wherein the pharmaceutical composition is in the form of an oral preparation, a parenteral preparation, or an external preparation.

11. The method according to claim 1, wherein the psoriasis is selected from the group consisting of psoriasis vulgaris, arthritic psoriasis, pustular psoriasis, and erythrodermic psoriasis.

12. A glaucocalyxin A derivative having the structure of formula I':

Formula I' wherein $R_1$ and $R_2$ are independently amino, cyclohexyl, alkyl, alkenyl, aryl, or heteroaryl.

13. The glaucocalyxin A derivative according to claim 12, wherein $R_1$ and $R_2$ are independently methyl, ethyl, n-propyl, isopropyl, n-butyl, t-butyl, isobutyl, n-heptyl, n-octyl, 2-pyridyl, 3-pyridyl, 4-pyridyl, n-hexyl, allyl, cyclohexyl, phenyl, or benzyl.

14. The glaucocalyxin A derivative according to claim 12, which has any one of the following Formulas If, In, Io, or Ip:

Formula If

Formula In

-continued

Formula Io

Formula Ip

15. A pharmaceutically acceptable salt of the glaucocalyxin A derivative according to claim 12, wherein the pharmaceutically acceptable salt is an organic or inorganic acid salt of the glaucocalyxin A derivative.

16. The pharmaceutically acceptable salt of glaucocalyxin A derivative according to claim 15, wherein the organic acid salt is any one selected from the group consisting of tartrate, stearate, oxalate, citrate, lactate, sorbate, fumarate, formate, acetate, benzoate, besylate, ethane sulfonate, resinate, trifluoroacetate, maleate, methanesulfonate, fumarate, amino acid salt, and nicotinate.

17. The pharmaceutically acceptable salt of glaucocalyxin A derivative according to claim 15, wherein the inorganic acid salt is any one selected from the group consisting of iodate, phosphate, sulfate, hydroiodide, hydrobromide, nitrate, bromate, and hydrochloride.

18. A method for preparing the glaucocalyxin A derivative according to claim 12, comprising reacting 2-bromoglaucocalyxin A with N,N-dialkylthiourea to provide a glaucocalyxin A derivative of formula I'.

* * * * *